United States Patent
Ramaiah et al.

(10) Patent No.: US 9,040,687 B2
(45) Date of Patent: May 26, 2015

(54) PROCESS FOR THE PREPARATON OF NOVEL PORPHYRIN DERIVATIVES AND THEIR USE AS PDT AGENTS AND FLUORESCENCE PROBES

(75) Inventors: Danaboyina Ramaiah, Thiruvananthapuram (IN); Suneesh C. Karunakaran, Thiruvananthapuram (IN); Jisha S. Vadakkancheril, Thiruvananthapuram (IN); Chandrashekar K. Tavarekere, Bhubaneswar (IN); Srinivasan Alagar, Bhubaneswar (IN); Madhavan Radhakrishna Pillai, Thiruvananthapuram (IN); Sivakumari Asha Nair, Thiruvananthapuram (IN); Saneesh Babu P. Saras, Thiruvananthapuram (IN); Mohan Chintalagiri Rao, Hyderabad (IN); Kunchala Sridhar Rao, Hyderabad (IN)

(73) Assignee: COUNCIL OF SCIENTIFIC AND IDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 13/574,512
(22) PCT Filed: Jan. 21, 2011
(86) PCT No.: PCT/IB2011/000085
§ 371 (c)(1), (2), (4) Date: Jul. 20, 2012
(87) PCT Pub. No.: WO2011/089509
PCT Pub. Date: Jul. 28, 2011

(65) Prior Publication Data
US 2012/0308485 A1    Dec. 6, 2012

(30) Foreign Application Priority Data
Jan. 22, 2010 (IN) .............................. 124/DEL/2010

(51) Int. Cl.
*C07D 487/22* (2006.01)
(52) U.S. Cl.
CPC .................... *C07D 487/22* (2013.01)
(58) Field of Classification Search
CPC .................................................. C07D 487/22
USPC .......................................................... 540/145
See application file for complete search history.

Primary Examiner — Brian McDowell
(74) Attorney, Agent, or Firm — Locke Lord LLP; Jeffrey D. Hsi

(57) ABSTRACT

The present invention provides novel porphyrin derivatives represented by the general formula 1 and/or pharmaceutically acceptable derivatives thereof as NIR sensitizers for photodynamic therapeutic and diagnostic, biological and industrial applications. These porphyrin derivatives possess absorption (400-700 nm) and emission (600-750 nm) in the regions where biological chromophores do not absorb and hence are ideal candidates for application as NIR PDT agents and fluorescence sensors for medicinal applications in biology. The substituents like hydroxyl and glycolic units on these dyes render them amphiphilicity thereby improving their solubility in the aqueous media and cellular uptake and localization. These dyes show no toxicity in the dark and are highly selective towards tumor cells and stain nucleus very rapidly. Accordingly, these porphyrin derivatives are extremely useful as NIR PDT fluorescence sensors in photodynamic therapeutic and diagnostic, biological and industrial applications.

Formula 1

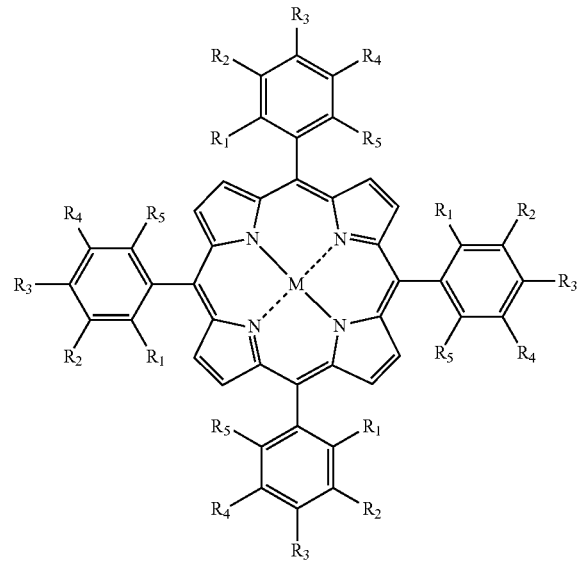

5 Claims, 6 Drawing Sheets

MDAMB cell lines

Figure 1:
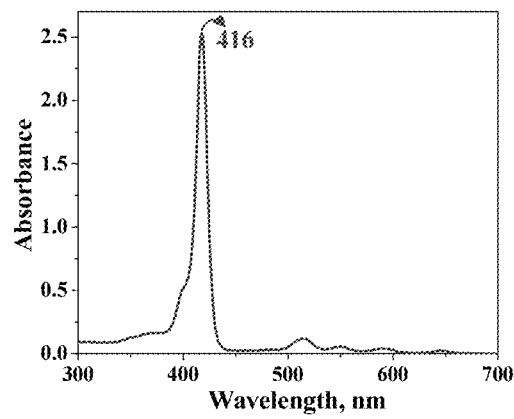

MDAMB cell lines
with porphyrins of the
general formulae 1

Merged

Stained with porphyrin of the general formulae 1

Stained with Hoechst 20X

Merged

PROCESS FOR THE PREPARATON OF NOVEL PORPHYRIN DERIVATIVES AND THEIR USE AS PDT AGENTS AND FLUORESCENCE PROBES

CROSS REFERENCE TO RELATED APPLICATIONS

This application is the national phase under 35 U.S.C. §371 of PCT International Application No. PCT/IB2011/000085, filed Jan. 21, 2011, which claims the benefit of Indian Patent Application No. 124/DEL/2010, filed Jan. 22, 2010, the entire contents of the aforementioned applications are hereby incorporated herein by reference.

FIELD OF INVENTION

The present invention relates to porphyrin derivatives useful as PDT agents and near infrared (NIR) fluorescence probes in photodynamic therapeutic, diagnostic, and biological, biochemical and industrial applications. More particularly, the present invention also relates to a process for the preparation of porphyrin derivatives of the general formula 1 and their use as NIR fluorescence probes in photodynamic applications for the detection of cancer and other diseases in human beings or animals.

BACKGROUND OF THE INVENTION

Photodynamic therapy (PDT) is a fast developing modality for the diagnosis and treatment of both oncological and non-oneological diseases and it involves the use of photochemical reactions mediated though the interaction of photosensitizing agents, light, and oxygen for the treatment of malignant or benign diseases. PDT is a 2-step procedure. In the first step, the photosensitizer is administered to the patient by one of several routes (eg. topical, oral, intravenous), and it is allowed to be taken up by the target cells. The second step involves the activation of the photosensitizer in the presence of oxygen with a specific wavelength of light directed toward the target tissue. Because the photosensitizer is preferentially absorbed by hyperproliferative tissue and the light source is directly targeted on the lesional tissue, PDT achieves both selectivity, minimizing damage to adjacent healthy structures. References may be made to Lane, N. *Scientific American* 2003, 38, 45; Bonnett, R. *Chem. Soc. Rev.* 1995, 24, 19; Dougherty, T. J. *Photochem. Photobiol.* 1987, 45, 879; Kessel, D. Dougherty, T. *J. Phorphyrin Photosensitization*; Plenum Publishing Corp. New York, 1983; Bissonette, R.; Bergeron, A.; Liu, Y. d. *J Drugs. Dermatol.* 2004, 3, 26-31; Jeffes, E. W.; McCullough, J. L.; Weinstein, G. D.; Fergin, P. E.; Nelson, J. S.; Shull, T. F. *Arch. Dermatol*, 1997, 133, 727-732. The process requires the presence of a photosensitizing agent, which is capable of being taken up by target tissues and which, on irradiation by light of a particular wavelength, generates highly reactive species which are toxic to those tissues. Photodynamic therapy has advantages over many other conventional therapies due to the selectivity of the photodynamic process. There is more sensitizer in the tumor tissues than in the normal tissues; this reduces the potential for destruction of normal tissues. In addition the ability to direct light specifically onto the target cells and tissues by the use of fiber-optic technology further increased the selectivity of this process. Furthermore, the use of photosensitizing agents, which produce no response until irradiated with light, significantly reduces the potential for side effects. References may be made to Jeffes, E. W.; McCullough, J. L. Weinstein, G. D.; Kaplan, R.; Glazer, S. D.; Taylor, J. R. *J. Am. Acad. Dermatol*, 2001, 45, 96-104; Kurwa, H. A.; Yong-Gee, S. A.; Seed, P. T.; Markey, A. C.; Barlow, R. J. *J. Am. Acad. Dermatol*, 1999, 41, 414-8; Pariser, D. M.; Lowe, N. J.; Stewart, D. M,; Jarratt, M. T.; Lucky, A. W.; Pariser, R. J. *J. Am. Acad. Dermatol*, 2003, 48, 227-32.

In PDT, the detection of tumor tissue (diagnosis) is equally important when compared to the destruction via either apoptosis or necrosis of tumor cells (treatment). Near-infrared (NIR) dyes are presently attracting considerable interest as fluorescence probes for the detection of cancer. References may be made to Lin, Y.; Weissleder, R.; and Tung, C. H. *Bioconjugate Chem,* 2002 13, 605-610; Achilefu, S.; Jimenez, H. N.; Dorshow, R. B.; Bugaj, J. E.; Webb, E. G.; Wilhelm, R. R.; Rajagopalan, R.; Johler, J.; Erion, J. L. *J. Med. Chem.* 2002 45, 2003-2015; Mujumdar, S. R.; Mujumdar, R. B.; Grant, C. M.; Waggoner, A. S. *Bioconjugate Chem.* 1996, 7, 356-362. Since tissue is relatively transparent to NIR light, near infrared fluorescence imaging (NIRF) and PDT are capable of detecting and treating, respectively, even subsurface tumors. In this context the present invention aims at the development of efficient NIR absorbing fluorescent probes based on porphyrins for biological applications. We have synthesized porphyrin based molecules which exhibit absorption and emission in the NIR region and have substituents like hydroxyl and glycolic groups, which would render them amphiphilicity thereby increasing their solubility, fluorescence intensity and accelerating their cellular uptake.

In a diagnostic technique, a dye is administered and allowed to distribute in the body as in the case of the treatment technique. However, in addition to the tumor selectivity, the sensitizer in the diagnostic technique should exhibit significant fluorescence yields under physiological conditions. Hence the development of photosensitizers, which have strong absorption in the long wavelength region, non-toxic to normal tissues, soluble in buffer at physiological pH, and exhibit higher therapeutic efficacy are still desired. Also the design of functional molecules that can target specific cancer cells are extremely important because of the biochemical and biomedical applications.

Porphyrin molecules are one of the photosensitizers currently being investigated. Porphyrins are macrocyclic molecular compounds with a ring-shaped tetrapyrrolic core. References may be made to Mahler, H. R.; Cordes, E. H. *Biological Chemistry,* 2d ed. 1966, 418; Joni, G.; Reddi, E. *Int J Biochem,* 1993, 25, 1369-75. Wiehe, A.; Shaker, Y. M.; Brandt, J. C.; Mebs, S.; Senge, M. O. *Tetrahedron,* 2005, 61, 5535-5564; and Pushpan, S. K.; Venkatraman, S.; Anand, V. G.; Sankar, J.; Parameswaran, D.; Ganesan, S.; Chandrashekar, T. K. *Curr. Med. Chem.—Anticancer Agents,* 2002, 2, 187-207. As such, porphyrins are commonly found in their dianionic form coordinated to a metal ion. The unique properties of the tetrapyrrolic core have made porphyrin central in many biological systems that play a vital role in many life processes. Several compounds which are critically important for essential biological processes, such as chlorophyll and heme, are derived from the coordination of a metal ion with a porphyrin nucleus. Porphyrins are able to form metal chelates with a large variety of metal ions, including: cobalt, copper, iron, magnesium, nickel, silver, and zinc. Heme is an iron chelate of a porphyrin, while chlorophyll and bacteriochlorophyll are magnesium chelates. Porphyrin such as these is generally synthesized from the precursors glycine and suceinyl CoA. References may be made to L. Stryer, *Biochemistry,* $2^{nd}$ ed. 504-507 (1981). It has further been well established that the hydro- or Lipo-philicity of a photosensitizes strongly affects the binding of the photosensitizer to a target cell, and as a consequence, its cytotoxic activity. References may be made to Merehat et al., *J. Photochem. Photobiol. B: Biol.*, 35:149-157 (1996).

Currently known porphyrin based photosensitizers includes hematoporphyrin derivative (HpD) and photofrin called the first generation photosensitizers. HpD is facing the major drawbacks includes (a) it is a mixture of at least nine components, (b) preparation is highly sensitive to reaction conditions and (c) causes cutaneous photosensitivity. Another example of porphyrin based photosensitizer is 5, 10, 15, 20-tetrakis (meta-hydroxyphenyl)-chlorin which is commercially known as foscan. The current methods of their synthesis, and known techniques for their use are inadequate for many intended applications. References may be made to Konan, Y. N.; Cerny, R.; Favet, J.; Berton, M.; Gurny, R.; Alleman, E. *Eur. J. Pharm. Biopharm.* 2003, 55, 115-124; and Nawalany, K.; Rusin, A.; Kepczynki, M.; Mikhailov, A.; Kramer-Marek, G.; Snietura, M.; Poltowicz, J.; Krawcyzk, Z.; Nowakowska, M. *J. Photochem. Photobiol. B: Biology,* 2009, 97, 8-17. This is true in part due to the need for high concentrations of reagent and the requirement of extended irradiation periods. These factors render the methods burdensome and inconvenient. In addition, such conditions are not suitable for many medical and/or industrial applications. It is thus seen that there is a need for novel photosensitizing agents for medical or other applications. It would be an improvement in the art to provide an agent that utilizes a pathway for inactivating or killing an to organism which is non-mutagenic. Finally, it would be an additional improvement in the art to provide such a photosensitizer that is capable of functioning effectively at lower concentrations and over shorter periods than those currently known and taught in the art.

Our interest in this area originated from the idea of utilizing the derivatives of currently existing porphyrin derivatives for photodynamic applications. In recent years a great variety of non-porphyrinic sensitizers are being developed for use in PDT. Methylene blue, a red-light absorbing phenothiaxinium dye, has previously been used extensively as a biological assay stain and can be used in the clinical diagnosis of a variety of diseases and as a tumor marker in surgery. However, its use as an in vivo photosensitizer is limited by its reduction by ubiquitous cellular enzymes to the colorless form, which is photodynamically inactive. Rhodamine is an important laser dye and is being used in red light emitting laser dyes for a long time now. Because of their specific uptake by mitochondria and their known use as a biochemical fluorescent probe, rhodamine classes of molecules are being used as sensitizers in the treatment of malignant tumors. But on the other hand the readily available commercial dye, rhodamine 123 is a poor phototoxin because of its high fluorescence quantum yield, which leads to a low triplet quantum yield. References may be made to Yamamoto, H.; Okunaka, T.; Furukawa, K.; Hiyoshi, T,; Konaka, C.; Kato, H. *Curr. Sci,* 1999, 77, 894; Sharman, W. M.; Allen, C. M.; van Lier, J. E.; *Drug Discovery Today,* 1999, 4, 507; Milgrom, L.; MacRobert, S; *Chem. Britain,* 1998, 45; Bonnett, R. *Chem. Soc. Rev,* 1995, 24, 19. Dolphin, D. *Can. J. Chem,* 1994, 72, 1005.

Another class of molecules developed from our group for use in PDT is squaraines. Squaraines are a class of dyes possessing sharp and intense absorption in the near infrared region and exhibit significant triplet quantum yields. Among the various squaraine dyes developed, bis(3,5-diiodo-2,4,6-trihydroxyphenyl) squaraine is found to be a potential photosensitizer certainly possesses clinical applications though in vitro and in-vivo experiments. The dye is found to be a promising compound in PDT as an effective NM photosensitizer. References may be made to U.S. Pat. No. 6,770,787 B2; Ramaiah, D.; Joy, A.; Chandrasekar, N.; Eldho, N. V.; Das, S.; George, M. V; *Photochem. Photobio,* 1997, 65, 783-790; Ramaiah, D.; Eckert, 1.; Arun, K. T.; Weidenfeller, L.; Epe, B. *Photochem. Photobiol,* 2002, 76, 672-677.

Although there are several non-porphyrinic photosensitizers are available, the fact that a naturally occurring dye such as porphyrin is the drug of choice in PDT has prompted the search for better photosensitizers based on porphyrin macrocycle. These tetrapyrrole rings form a class of dyes possessing sharp and intense absorption bands in the visible to near infra red region. The photophysical and photochemical properties of these have been studied extensively, because their absorption and photochemical characteristics make them highly suitable for a number of biological and industrial applications. References may be made to U.S. Pat. No. 4,649,151; R. Bonnet, R. D. White, U. J. Winfield, M. C, Berenbaum. *Biochem. J.,* 1989, 261, 277-280; D. Kessel. *Photochem. Photobiol.,* 1984, 39, 851-859.

The novel porphyrin derivatives of the general formula 1 claimed in the current patent application are derivatives of tetraphenyl porphyrin. Preliminary investigations by us indicated that substitution of more number of hydroxy groups to the porphyrin meso-phenyl ring results in their increased solubility in the aqueous medium and enhanced intersystem crossing efficiency, when compared to the currently existing one. When compared to other porphyrins, which are not water soluble, the derivatives claimed in the present invention exhibit high water solubility.

More over, insertion of heavy metals like Zinc onto the porphyrin macrocycle also caused increased intersystem crossing efficiency and hence high singlet oxygen generation efficiency. These dyes exhibited absorption in the range from 400-700 nm and fluorescence emission in the range 600-800 nm. These dyes are having almost good fluorescence quantum yields in the range 0.15-0.23. Also the quantum yields of triplet excited states ($\Box_T$) of these porphyrin derivatives are found to be in the range 0.60-0.75 and the quantum yields of singlet oxygen generation ($\Box(^1O_2)$) in the range 0.40-0.75, depending on the nature of the substituent present on the mesa phenyl ring and the inserted metal. The cytotoxicity, mutagenicity, kinetics of uptake and release and the cellular localization studies of these porphyrin derivatives using mammalian cell lines and bacterial strains indicated that these dyes exhibit significant cytotoxicity upon excitation with visible light and the mechanism of their biological activity could be attributed to the in vitro generation of singlet oxygen.

Cellular localization studies of the synthesized porphyrin derivatives showed that they are preferentially accumulating on the nucleus with red fluorescence during visible light excitations. Hence these derivatives can be used as NIR fluorescent probes for nuclear staining. Most of the reported porphyrins such as chlorin e6 and to hematoporphyrin derivatives localize mainly at the plasma membrane, whereas, our photosensitizers that localize at the nucleus would be much more effective in producing photodynamic damage.

Cellular uptake studies on the porphyrin derivatives of the present invention showed that they are far more efficient. The novel porphyrin derivatives of the present invention show maximum cellular uptake within 10 min, which has been evidenced through the fluorescence microscopic images given as FIG. 10 while the cellular uptake of PhtofrinR is maximum only within 4 h.

Also the present investigation showed that the porphyrin derivatives have binding affinity towards proteins such as serum albumin and hence can be used as NIR fluorescent probes for protein labeling.

In the present invention we have synthesized novel porphyrin derivatives and demonstrated their, potential as NIR PDT agents and fluorescent probes for biological and biochemical applications.

OBJECTIVES OF THE INVENTION

The main objective of the present invention is to provide porphyrin derivatives useful as PDT agents and near infrared (NIR) fluorescence probes in photodynamic therapeutic, diagnostic, and biological, biochemical and industrial applications.

Another objective of the present invention is to provide porphyrin derivatives and or pharmaceutical acceptable derivatives thereof, for use as NIR fluorescence probes in photodynamic diagnostic applications for the detection of tumors.

Another objective of the present invention is to provide porphyrin derivatives and or pharmaceutical acceptable derivatives thereof, for use as near-infrared fluorescence sensors for biological, biochemical and industrial applications.

Yet another objective of the present investigation is to provide porphyrin derivatives that can be used as NIR fluorescent probes for protein labeling.

Yet another objective of the present investigation is to provide porphyrin derivatives that can be used as NIR fluorescent probes for nuclear staining.

Yet another objective of the present investigation is to provide porphyrin derivatives of the general formulae 1 that can be used as NIR fluorescent labels in immunoassays.

BRIEF DESCRIPTION OF THE ACCOMPANYING DRAWINGS

In the drawings accompanying the specifications

FIG. 1 Absorption spectra of porphyrin derivatives of the general formula 1 wherein, $R_1, R_3, R_5$=OH; $R_2, R_4$=H; M=2H in water.

Figure 2:
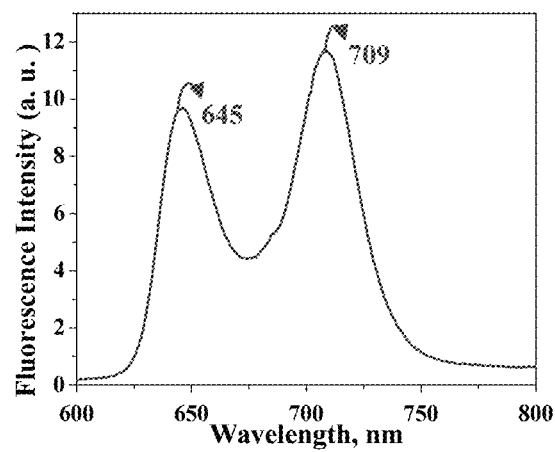

FIG. 2 Fluorescence emission spectra of porphyrin dyes of the general formula 1 wherein, $R_1, R_3, R_5$=OH; $R_2, R_4$=H; M=2H in water.

Figure 3:
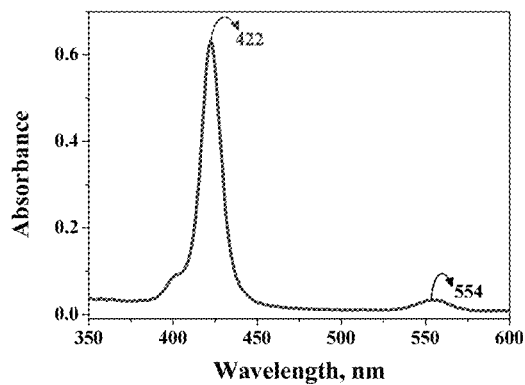

FIG. 3 Absorption spectra of porphyrin derivatives of the general formula 1 wherein, $R_1, R_3, R_5$=OH; $R_2, R_1$=H; M=Zn in water.

Figure 4:
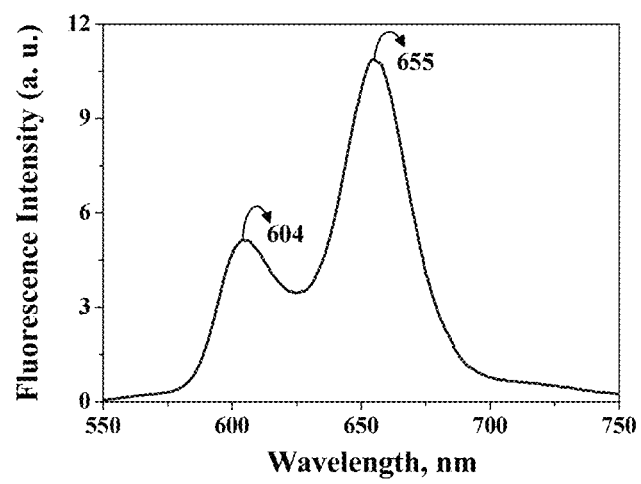

FIG. 4 Fluorescence emission spectra of porphyrin derivatives of the general formula 1 wherein, $R_1, R_3, R_5$=OH; $R_2, R_4$=H; M Zn in water.

Figure 5:
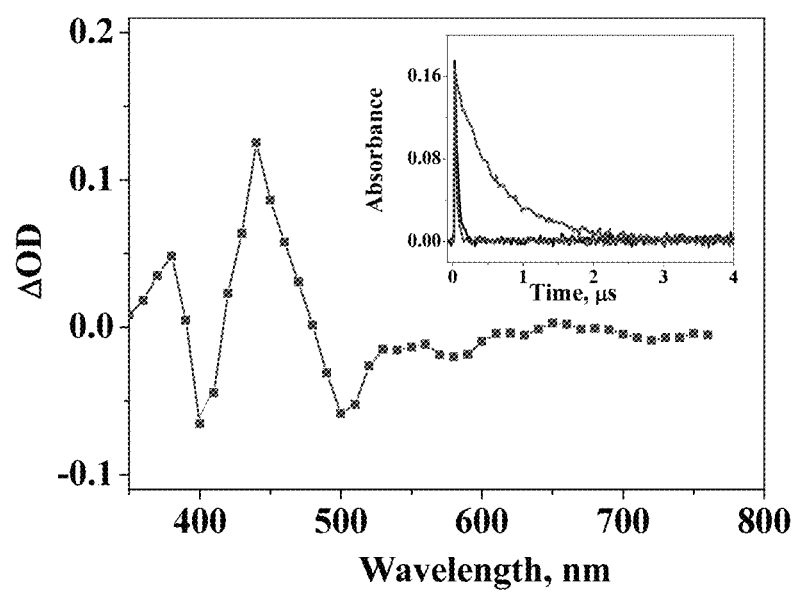

FIG. 5 Triplet absorption spectra of porphyrin derivatives of the general formula 1 wherein, $R_1, R_3, R_5$=OH; $R_2, R_4$=H; M=2H in methanol. Laser Excitation wavelength, 532 nm. Inset shows the transient decay profile at 440 nm of the porphyrin derivative of general formula 1, wherein, $R_1, R_3, R_5$=OH; $R_2, R_4$=H; M=2H in methanol in the absence and, presence of oxygen.

Figure 6A:
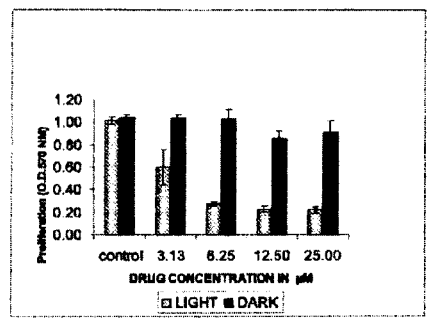
Figure 6B:
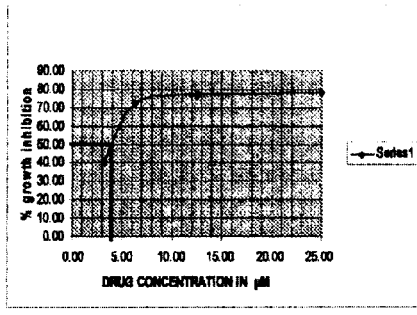

FIG. 6 (a) Histogram showing cytotoxicity of the investigated porphyrin derivative of general formula 1, wherein, $R_1, R_3, R_5$=OH; $R_2, R_1$=H; M=2H in oral cancer cells (SCC 131). Figure showing the cellular proliferation of human oral cancer cells (SCC131) after 48 h treatment with various concentration of the investigated porphyrin derivatives of the general formulae 1 with and with out irradiation using visible light from sodium vapor lamp (50 J/cm² 590 nm). (b) Plot of % growth inhibition of oral cancer cells (SCC 131) at various concentrations of porphyrin derivative of general formula 1, wherein, $R_1, R_3, R_5$=OH; $R_2, R_4$=H; M=2H. Data give the % growth inhibition after 48 h treatment with various concentration of porphyrin derivative of general formula 1, wherein, $R_1, R_3, R_5$=OH; $R_2, R_4$=H; M=2H with visible light from sodium vapor lamp (50 J/cm² 590 nm).

Figure 7A:
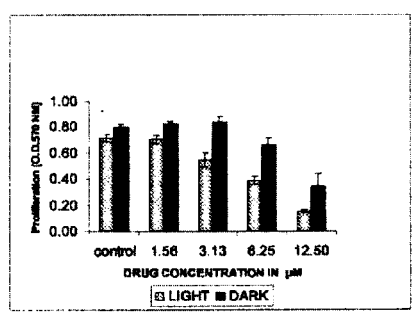
Figure 7B:
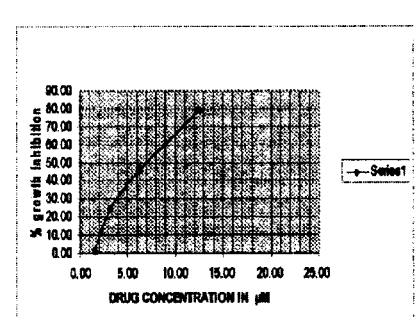

FIG. 7 (a) Histogram showing cytototoxicity of the investigated porphyrin derivative of general formula 1, wherein, $R_1, R_3, R_5$=OH; $R_2, R_4$=H; M=2H in mammalian breast cancer cells (MDAMB). Figure showing the cellular proliferation of mammalian breast cancer cells (MDAMB) after 48 h treatment with porphyrin derivatives of the general formula 1 with and with out irradiation using visible light from sodium vapor lamp (50 J/cm² 590 nm). (b) Plot of % growth inhibition of mammalian breast cancer cells (MDAMB) at various concentrations of porphyrin derivative of general formula 1, wherein, $R_1, R_3, R_5$=OH; $R_2, R_4$ H; M=2H. Data give the % growth inhibition after 48 h treatment with various concentration of porphyrin derivative of general formula 1, wherein, $R_1, R_3, R_5$=OH; $R_2, R_4$=H; M=2H with visible light from sodium vapor lamp (50 J/cm² 590 nm).

Figure 8:
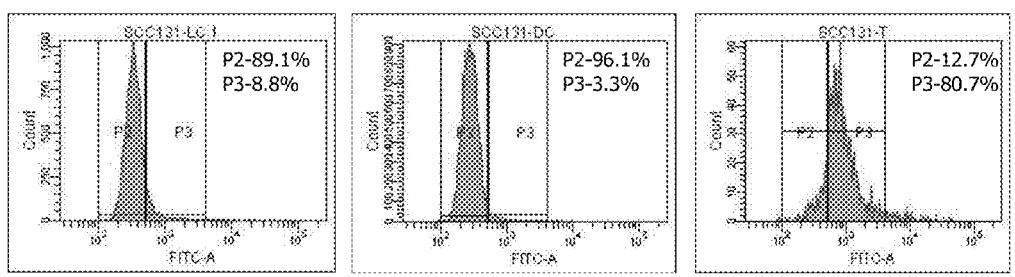

FIG. 8 Histogram showing the mechanism of cell death in oral cancer cells (SCC 131) with porphyrin derivative of general formula 1, wherein, $R_1, R_3, R_5$=OH; $R_2, R_4$=H; M=21-1 by FACS analysis in. Apoptotic population (P3) shows a right shift in the FACS histogram plotted against cell count vs. FITC staining FIG. 9 Fluorescence microscopic images of the mammalian breast cancer cells (MDAMB 231) after incubation with the investigated porphyrin derivative of the general formula 1 wherein, $R_1, R_3, R_5$=OH; $R_2, R_4$=H; M=2H showing intake of porphyrin derivatives of the general formula 1 wherein, $R_1, R_3, R_5$=OH; $R_2, R_4$=H; M=2H by the cancer cells within a short time period, here with in one hour. The merged picture confirms presence of drug inside the cells.

Figure 10:
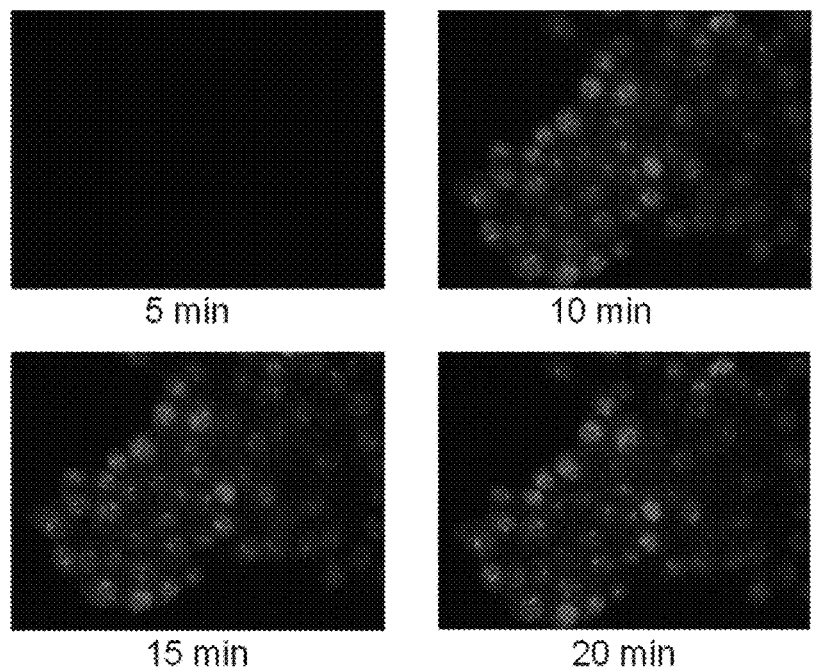

FIG. 10 Fluorescence microscopic images of the oral cancer cells (SCC 131) with porphyrin derivative of the general formula 1 wherein, $R_1, R_3, R_5$=OH; $R_2, R_4$=H; M=2H at different time intervals of 5 min. showing intake of porphyrin derivatives of the general formula 1 wherein, $R_1, R_3, R_5$=OH; $R_2, R_4$=H; M=2H by the cancer cells within a short time period, here with in 10 min.

Figure 11:
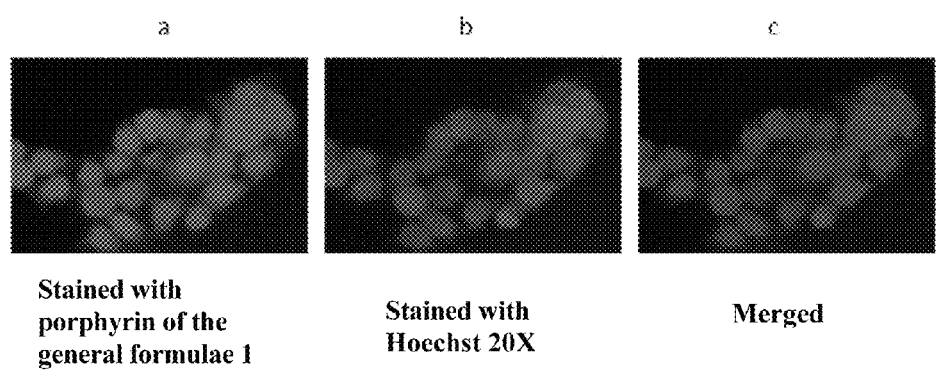

FIG. 11 Nuclear staining of the mammalian breast cancer (MDAMB231) cells (a) after incubation with the investigated porphyrin derivatives of the general formulae 1 wherein, $R_1, R_3, R_5$=OH; $R_2, R_4$=H; M=2H, (b) after incubation with Hoechst (a commercially available nuclear dye) and (c) shows the merged image of a and b.

SUMMARY OF THE INVENTION

Accordingly, the present invention relates to porphyrin derivatives useful as PDT agents and near infrared (NIR) fluorescence probes in photodynamic therapeutic, diagnostic, and biological, biochemical and industrial applications.

In one embodiment of the invention, Porphyrin derivatives of the general formulae 1, Formula 1

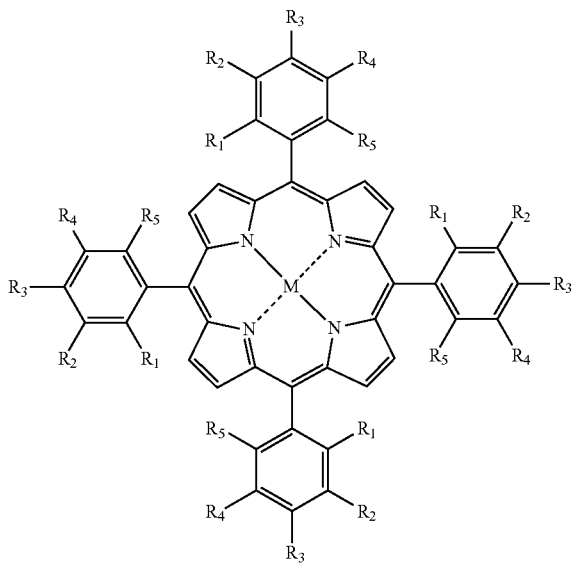

Wherein, $R_1$, $R_3$, $R_5$=OH; $R_2$, $R_4$=H; M=2H
Wherein, $R_1$, $R_3$, $R_5$=OH; $R_2$, $R_4$=H; M=Zn, Co, Cu, Fe, Au
Wherein, $R_1$, $R_3$, $R_5$=OH; $R_2$, R.; I; M=2H
Wherein, $R_1$, $R_3$, $R_5$=OH; $R_2$, $R_4$=I; M=Zn, Co, Cu, Fe, Au
Wherein, $R_1$, $R_2$, $R_4$, $R_5$=H; $R_3$=(OCH$_2$CH$_2$)$_n$OH (where n=3-7); M=2H
Wherein, $R_1$, $R_2$, $R_4$, $R_5$=H; $R_3$=(OCH$_2$CH$_2$)$_n$OH (where n=3-7); M=Zn, Co, Cu, Fe, Au.

In another embodiment of the present invention, a process for the preparation of porphyrin derivatives of general formulae 1, wherein the said process comprises:
a. mixing 2,4,6-trimethoxy or 4-(triethylene glycol) substituted benzaldehyde with pyrrole in the ratio 1:25 mmol followed by stirring under inert atmosphere and light protection for a period ranging between 15-20 min at temperature ranging between 25-30° C.;
b. adding trifluoroacetic acid drop by drop into the reaction mixture as obtained in step (a) followed by restirring for a period ranging between 20-30 min;
c. quenching the mixture as obtained in step (b) by adding a solvent;
d. neutralizing the excess trifluoroacetic acid from the reaction mixture as obtained in step (c) by sodium hydroxide solution;
e. separating the organic layer from the reaction mixture as obtained in step (d) followed by washing with water and drying over anhydrous sodium sulphate to get anhydrous organic layer;
f. concentrating organic layer as obtained in step (e) under reduced pressure to get viscous material;
g. chromatographing the viscous material as obtained in step (f) over silica gel with mixture of ethyl acetate and hexane (2:8) to obtain 2,4,6-trimethoxy or 4-(triethylene glycol) substituted phenyldipyrromethane;
h. dissolving 2,4,6-trimethoxy or 4-(triethylene glycol) substituted phenyldipyrromethane as obtained in step (g) with 2,4,6-trimethoxy or 4-(triethylene glycol) substituted benzaldehyde in a solvent;
i. adding trifluoroacetic acid slowly into the mixture as obtained in step (h) followed by stirring at temperature ranging between 25-30° C.;
j. adding 2,3-dichloro-5,6-dicyanobenzoquinone (DDQ) into the mixture as obtained in step (i) followed by stirring at temperature ranging between 25-30° C. for a period ranging between 1-3 h;
k. pouring the reaction mixture as obtained in step (j) onto a pad of alumina and eluted with solvent followed by removing the solvent under pressure to obtain a black solid;
l. chromatographing the black solid as obtained in step (k) over silica gel with methylene chloride to obtain porphyrin derivative.

In yet another embodiment of the invention, solvent used in steps (c), (h) and (k) are selected from the group consisting of methylene chloride and chloroform.

In yet another embodiment of the present, Porphyrin derivatives are useful in the near-infrared fluorescence sensors for photodynamic, diagnostic, biological and industrial applications.

In yet another embodiment of the present invention, Porphyrin derivatives are useful as NIR fluorescence probes in photodynamic applications for the detection of cancer and other diseases in human beings or animals.

In another embodiment of the present invention, Porphyrin derivatives are useful as near-infrared fluorescence probes for biological applications such as protein labeling, nuclear staining under visible light radiation.

In yet another embodiment of the present invention, Porphyrin derivatives are useful as NIR fluorescent labels in immunoassays under visible light radiation.

In yet another embodiment of the present invention, Porphyrin derivatives are useful under harmless radiations.

DETAILED DESCRIPTION OF THE INVENTION

In the present invention, porphyrin derivatives of the general formulae 1 have been synthesized. Modification using glycol moieties is expected to render amphiphilicity to these dyes and hence increase the cell permeability and to bring about target specificity Examples 1-4 represent typical synthesis of compounds of the general formulae 1 and examples 5-7 represent the in vitro evaluation of the porphyrin derivative of general formula 1, wherein $R^1$=R2=$R_3$=OH, M=2H for photodynamic therapy using mammalian cancer cells.

The following examples are given by way of illustration and therefore should not be construed to limit the scope of present investigation.

EXAMPLE 1

Preparation of the porphyrin derivative of general formula 1, wherein $R_1$=$R_3$=$R_5$=OH, $R_2$=$R_4$=H or T, M=2H. 2,4,6-trimethoxybenzaldehyde (5.1 mmol) was added to distilled pyrrole (127 mmol) and stirred under argon atmosphere and light protection to for 15 min. Trifluoroacetic acid (0.5 mmol) was added drop by drop to the reaction mixture and again stirred for 20 min). The reaction was quenched by adding methylene chloride (25 mL) and excess trifluoroacetic acid was neutralized with sodium hydroxide solution. Separated the organic layer and washed it with distilled water, dried over anhydrous sodium sulphate and concentrated under reduced pressure. The viscous material obtained was chromatographed over silica gel. Elution of the column with a mixture of ethyl acetate and hexane (2:8) gave 75% of 2,4,6-trimethoxyphenyldipyrromethane. nip 120-122° C.; $^1$H NMR (500 MHz, CDCl$_3$, 30° C., TMS); δ=3.72 (s, 6H, —OCH$_3$), 3.79 (s, 3 H, —OCH$_3$), 5.55 (s, 1H, —CH), 5.88-5.89 (d, 2H, J=8.00 Hz, Ar-pyrrole-H), 6.07-6.09 (d, 214, J=8.5 Hz, Ar- Pyrrole-H), 6.11-6.6.23 (d, 2H, J=8.5 Hz, Ar-pyrrole-H), 6.61-6.62 (d, 214, J=7.0 Hz, Ar—H), 8.46 (s, 2H, Pyrrole-NH); $^{13}$C NMR (125 MHz, CDCl$_3$, 30° C., TMS): δ=30.95, 32, 32, 37.32, 55.37, 56.40, 92.47, 105.70, 106.73, 107.72, 108.54, 112.22, 116.05, 117.32, 131.13, 133.38, 158.88, 160.08; IR (Neat): $v_{max}$ 3375, 1593, 1463, 1413, 1313, 1219, 945 cm$^{-1}$; FAB-MS: m/z=312.56 (calcd 312.36 for $C_{18}H_{20}N_2O_3$).

2,4,6-Trimethoxyphenyldipyrromethane (3.2 mmol) and 2,4,6-trimethoxybenzaldehyde (3.2 mmol) were dissolved in dry methylene chloride (500 mL) in a 1 L round-bottomed flask, and trifluoroacetic acid (1.3 mmol) was added slowly over 15 min, The reaction mixture was allowed to stir under argon atmosphere for 2 h at 30° C. After 2 h, 2,3-dichloro-5, 6-dicyanobenzoquinone (DDQ) (4.8 mmol) was added, and the reaction mixture was stirred at 30° C. for 2 h. The complete reaction mixture was poured onto a pad of alumina (50 mm maximum diameter×150 mm length) and eluted with methylene chloride (ft). The solvent was removed under reduced pressure to give a black solid, which was chromatographed over silica gel. Elution of the column with methylene chloride gave 25% of 5, 10, 15, 20-(2,4,6-trimethoxyphenyl) porphyrin. mp>300° C.; $^1$H NMR (500 MHz, CD$_2$Cl$_2$, 30° C., TMS): δ 3.48 (s, 24H, —OCH$_3$), 4.20 (s, 12H, —OCH$_3$), 6.52 (s, 8H, —Ar—H), 8.64 (s, 8H, Ar—H, pyrrole); IR (Neat): $v_{max}$ 2949, 2794, 1660, 1600, 1573, 1556, 1462, 1411, 1334 cm$^{-1}$; elemental analysis calcd (%) for $C_{36}H_{52}N_2O_{10}$: C, 68.98; H, 5.58; N, 5.75; found: C, 67.44; H, 5.88; N, 5.23; MALDI-TOF-MS: m/z=975.22 (calcd 974.37 for $C_{56}H_{54}N_4O_{12}$).

Boron tribromide (7.4 mmol) was added to dry distilled methylene chloride (10 mL) and the mixture was cooled to −78° C. The apparatus was fitted with a calcium chloride drying tube. 5, 10, 15, 20-(2,4,6-trimethoxyphenyl)porphyrin (0.3 mind) was dissolved in minimum volume of dry methylene chloride (10 ml), placed in a dropping funnel and slowly added over a period of 20 min. The mixture was stirred for 2 h at −78° C. and then for 12 h at 25° C. After cooling to 0° C. with an ice bath, excess of methanol was added to solvolyse any excess of Boron tribromide and to breakdown the porphyrin-boron tribromide complex. Triethylamine was added to neutralize the reaction mixture and concentrated under reduced pressure to give an amorphous purple solid, which was recrystallized from a mixture of methanol and chloroform to give 70% of the porphyrin derivative of the general formula 1, wherein, $R_1$=$R_3$=$R_5$=OH, M=2H, mp>300° C.; $^1$H NMR (500 MHz, DMSO-d$_6$, 30° C., TMS): δ=6.268 (s, 8H, Ar—H), 8.746 (s, 8H, —Ar—H, pyrrole), 9.016 (d, 81-1, —Ar—OH), 9.388 (s, 4H, —Ar—OH); $^{13}$C NMR (125 MHz, CD$_3$OD, 30° C., TMS): δ=93.94, 94.18, 98.60, 103.92, 108.58, 113.22, 115.23, 131.05, 132.19, 132.84, 139.15, 146.76, 158.63, 159.06; IR (Neat): $v_{max}$ 3280, 2948, 1614, 1584, 1469, 1348, 1047 cm$^{-1}$; MALDI-TOF-MS: m/z 808.97 (calcd 806.72 for $C_{44}H_{30}N_4O_{12}$).

EXAMPLE 2

Preparation of the porphyrin derivative of general formula 1, wherein $R_1$=$R_3$=$R_5$=OH, $R_2$=$R_4$=H or 1, M=Zn. A solution of the porphyrin derivative of the general formula 1, wherein, $R_1$=$R_3$=$R_5$=OH, M =2H(0.62 mmol) in a mixture of 25 mL of methnol and chloroform (1:2) was refluxed with Zinc acetate (3.1 mmol) for 6 h. The solvent was distilled off under reduced pressure and the residue obtained was washed with several portions of distilled water to remove the excess Zinc acetate. The crude material obtained was recrystallized from a mixture of methanol and chloroform to get 85% of the porphyrin derivative of the general formula 1, wherein, $R_1$=$R_3$=$R_5$=OH, M=Zn, mp>300° C.; NMR (500 MHz, DMSO-d$_6$, 30° C., TMS): δ=6.24 (s, 8H, Ar—H), 8.69 (s, 8H, —OH), 8.74 (s, 8H, Ar-pyrrole-H), 9.26 (s, 4H, —OH); $^{13}$C NMR (125 MHz, CD$_3$OD, 30° C., TMS): δ=9394, 94.18, 98.60, 103.92, 108.58, 113.22, 115.23, 131.05, 132.19, 132.84, 139.15, 146.76, 158.63, 159.06; IR (Neat): $v_{max}$ 3281, 1614, 1469, 1151, 1047 cm$^{-1}$; MALDI-TOF-MS: m/z=865.76 (calcd 65.85 for $C_{44}H_{28}N_4O_{12}Zn$).

EXAMPLE 3

Preparation of the porphyrin derivative of general formula 1, wherein $R^1$=$R2$=$R_3$=$R_5$=H, $R_3$=$PC_{1-2}CH_2)_3$OH, M=2H. 4-(triethylene glycol) benzaldehyde (3.9 mmol) was added to distilled pyrrole (98.3 mmol) and stirred under argon atmosphere and light protection for 15 min. Trifluoroacetic acid (0.39 mmol) was added drop by drop to the reaction mixture and again stirred for 20 min. The reaction was quenched by adding methylene chloride (20 mL) and excess trifluoroacetic acid was neutralized with sodium hydroxide solution. Separated the organic layer and washed it with distilled water, dried over anhydrous sodium sulphate and concentrated under reduced pressure. The viscous material obtained was chromatographed over silica gel. Elution of the column with a mixture of ethyl acetate and hexane (1:1) gave 80% of 4-(triethyleneglycol)phenyldipyrromethane. mp 100-102° C.; $^1$H NMR (300 MHz, CDCl$_3$, 30° C., TMS): δ=3.47 (t, 2H, —CH$_2$), 3.66 (t, 2H, —OCH$_2$), 4.07 (m, 6H, —OCH$_2$), 4.20 (t, 2H, —OCH$_2$), 5.45 (s, 1H, —CH), 5.89 (d, 2H, 8.00 Hz, Ar-pyrrole-H), 6.09 (d, 2H, J=8.5 Hz, Ar—Pyrrole-H), 6.6.23 (d, 21-1, J=8.5 Hz, Ar-pyrrole-H), 7.02 (d, 2H, J=8.6 Hz, Ar—H), 7.81 (d, 21-1, J=8.6 Hz, Ar—H), 8.51 (s, 2H, Pyrrole-NH); $^{13}$C NMR (125 MHz, CDCl$_3$, 30° C., TMS): δ=43.7, 61.3, 69.3, 70.0, 70.2, 107.3, 108.3, 114.0, 118.3, 129.0, 130.1, 155.9; IR (Neat): $v_{max}$ 3442, 3415, 2877, 1600, 1584, 1257, 651 cm$^{-1}$; FAB-MS: m/z=370.36 (calcd 370.44 for $C_{21}H_{26}N_2O_4$).

4-(Triethyleneglycol)phenyldipyrromethane (2.7 mmol) and 4-(triethylene glycol)benzaldehyde (2.7 mmol) were dissolved in dry methylene chloride (450 ml) in a 1 L round-bottomed flask, and then trifluoroacetic acid (1.1 mmol) was added slowly over 60 seconds. The reaction mixture was stirred at 30° C. After 1 h, 2,3-dichloro-5,6-dicyanobenzoquinone (DDC) (4 mmol) was added, and the reaction mixture was stirred at 30° C. for further 1 h. The complete reaction mixture was poured onto a pad of alumina (50 mm maximum diameter×150 mm length) and eluted with methylene chloride (1 L), followed by a mixture of methanol and chloroform (1:1). The solvent was removed under reduced pressure to give a black solid, which was chromatographed over silica gel. Elution of the column with a mixture of methanol and chloroform (1:19) gave 28% of 5, 10, 15, 20-(4-(triethyleneglycol) phenyl)porphyrin. mp>300° C.; $^1$H NMR (300 MHz, CDCl$_3$, 30° C., TMS): δ=−2.76 (s, 2H, Pyrrole-NH), 3.71-3.90 (m, 24H, —CH$_2$), 4.08 (t, 8H, —C$_{1-12}$), 4.32 (t, 81-1, —CH$_2$), 4.45 (t, 8H, —OCH$_2$), 7.31 (d, 8H, 8.5, —ArH), 8.12 (d, 8H, J=8.4, —ArH); $^{13}$C NMR (125 MHz, CDCl$_3$, 30° C., TMS): δ=61.84, 67.67, 70.32, 70.46, 112.86, 114.97, 119.70, 126.23, 126.85, 131.42, 134.92, 135.56, 158.53; IR (Neat): $v_{max}$ 3311, 2875, 1604, 1506, 1350, 1246, 966 cm$^{-1}$; MALDI-TOF-MS: m/z=1207.7 (calcd 1207.36 for $C_{68}H_{78}N_4O_{16}$).

EXAMPLE 4

Preparation of the porphyrin derivative of general formula 1, wherein $R^1$=$R2$=$R_4$=$R_5$=H, $R_3$=(OCH$_2$CH$_2$)$_3$OH, M=Zn.

A solution of the porphyrin derivative of the general formula 1 (0.41 mmol) in dry chloroform (20 mL) was refluxed with Zinc acetate (2.1 mmol) for 5 h. The solvent was distilled off under reduced pressure and the residue obtained was washed with several portions of distilled water to remove the excess Zinc acetate. The crude material obtained was recrystallized from a mixture of methanol and chloroform to get 92% of the porphyrin of the general formula 1, wherein, $R^1=R_2=R_4=R_5=H$, $R_3=(OCH_2CH_2)_3OH$, M=Zn, mp>300° C.; $^1H$ NMR (300 MHz, CDCl$_3$, 30° C., TMS): 3.71-3.90 (m, 241-1, —CH$_2$), 4.08 (t, 4.32 (t, 8H, —CH$_2$), 4.45 (t, 8H, —OCH$_2$), 7.28-7.31 (d, 8H, J=8.5, —ArH), 8.12 (d, 8H, J=8.4, —ArH); $^{13}C$ NMR (125 MHz, CDCl$_3$, 30° C., TMS): δ=61.84, 67.67, 70.32, 70.46, 112.86, 114.97, 119.70, 126.23, 126.85, 131.42, 134.92, 135.56, 158.53; IR (Neat): $v_{max}$ 3416, 2875, 1604, 1506, 1350, 1246, 681 cm$^{-1}$; MALDI-TOF-MS: m/z=1266.33 (calcd 1265.48 for $C_{68}H_{76}N_4O_{12}Zn$).

EXAMPLE 5

Determination of Cytotoxicity by Measuring Cellular Proliferation.

3, (4,5-Dimethylthiazol-2-yl)-2,5-diphenyltetrazolium bromide (MTT) assay is a standard colorimetric assay for measuring cellular proliferation (cell growth). It was used to determine cytotoxicity of the porphyrin derivatives of the general formulae 1. Human cervical oral cancer cells (SCCl$_{31}$ cells) (5×10$^3$ cells well$^{-1}$) were added to wells of two 96 well microtiter plate. One for dark cytotoxicity and another for light cytotoxicity with 150 μL DMEM (Dulbecco's Modified Eagle Medium) with 10% serum and incubated for 24 h. Then added 3.125 to 25 μM of porphyrin derivatives of the general formulae 1 in serial dilution (stock 100 mM diluted using DPBS (Dulbecco's Phosphate Buffered Saline) for test, 0.025% DMSO (dimethyl sulphoxide) for control and incubated for 3 h and irradiated in one plate using sodium vapor lamp (70 w for 15 min) while the other plate was kept in dark. After photoirradiation, DPBS was aspirated and 150 μL DMEM with 10% serum was added to each well and incubated is for 48 h. After 48 h of incubation, removed the plates from the incubator and added 10 μL of MIT (5 mg/ml stock) to each well of the plate. After 4 h, carefully removed the supernatant taking care that the formazan crystals formed are not being removed and added 100 μL of isopropyl alcohol to each well. Covered the plates with aluminium foil and kept on a shaker until the crystals are dissolved. Read the absorbance at 570 nm.

Percentage growth inhibition was calculated as %
Growth inhibition=(control-test)/control×100

FIG. 6.A showing cell proliferation after 48 hrs on various treatment concentration of porphyrin derivative of the general formulae 1 (3.125, 6.25, 12.5 & 25 μM) in oral cancer cells (SCC 131) with and without irradiation with 70 W sodium vapor lamp (590 nm). From the bar diagram it is evident that in the absence of irradiation there is no significant growth inhibition.

FIG. 6.B showing % growth inhibition after 48 hrs on various treatment concentration of porphyrin derivative of the general formulae 1 (3.125, 6.25, 12.5 & 25 μM) in oral cancer cells (SCC 131). From this porphyrin derivative of the general formulae 1 showed an IC$_{50}$ value of 4 μM FIG. 7.A showing cell proliferation after 48 hrs on various treatment concentration of porphyrins of the general formulae 1 (3.125, 6.25, 12.5 & 25 μM) in Breast cancer cells (MDA MB 231) with and without irradiation with 70 w sodium vapor lamp (590 nm). From the bar diagram it is evident that in the absence of irradiation there is no significant growth inhibition.

FIG. 7.B showing % growth inhibition after 48 hrs on various treatment concentration of porphyrins of the general formulae 1 (3.125, 6.25, 12.5 & 25 μM) in Breast cancer cells (MDA MB 231). From this graph, porphyrin derivative of the general formulae 1 showed an IC$_{50}$ value of 7 μM.

Comparative in vitro cytotoxicity study of porphyrin derivative of general formula 1, wherein $R_1=R_3=R_5=OH$, M=2H Vs Foscan as Standard Photosensitizer:

In order to understand the efficiency of the newly developed porphyrin derivatives as sensitizers in photodynamic therapeutic action, we have compared the cytotoxicity porphyrin derivative of general formula 1, wherein $R_1=R_3=R_5=OH$, M=2H with the commercial photosensitizer (Foscan). The cytotoxicity exhibited by these molecules has been examined through the well MTT assay, both in the presence and absence of light. The photosensitizing efficiency of these molecules has been evaluated by comparing the IC$_{50}$ values in both dark and light, and these results have been summarized in Table 1 as given below. From the IC$_{50}$ values obtained, it is clear that these molecules showed better cytotoxicity in the light when compared to the Foscan, which is now in commercial use.

|  |  | IC$_{50}$ Value | |
| --- | --- | --- | --- |
| S. No | Cell Line | Porphyrin derivative of general formula 1 | FOSCAN |
| 1 | HCT 116 | 6.5 | 9 |
| 2 | MCF 7 | 9 | 13 |
| 3 | HaCaT | 8 | 8 |
| 4 | MDA MB 231 | 6.5 | 13.5 |
| 5 | SCC 131 | 8.5 | 16 |
| 6 | SCC 172 | 8 | 12.5 |
| 7 | Mia PaCa | 10 | 11 |
| 8 | SiHa | 25 | 22.5 |
| 9 | HeLa | 18 | 22 |

EXAMPLE 6

Determination of Implode Assay by Cytometry.

Annexin V-conjugated to fluorochome such as FITC was used for the easy, flow cytometric identification of cells in the early stages of apoptosis. Three 60 mm plate were taken and SCC 131(2×10$^5$ cells per plate) were seeded with 2 mL DMEM medium and incubated for 24 h. One plate for Light control (without Drug) and one plate was taken as dark (with drug without light) control and remaining one for test (Drug±light). Then porphyrin derivatives of the general formulae 1 at a concentration of 25 μM (stock 100 mM. diluted using DPBS) was added to two plates and for third added 0.025% DMSO and incubated for 3 h and later photoirradiated two plates (Light control & Test) using sodium vapor lamp (70 w, 590 nm) for 15 min. After photoirradiation, DPBS was aspirated and 150 ul DMEM with 10% serum was added to each 35 mm plates and incubated for 48 h. After 48 h the cells were trypsinized and centrifuged and the pellet washed using 1×PBS and 200 μl of binding buffer was added to pellet. Filtered to flow cytometric tubes. 3 μL Annexin V-FITC was added and vortexed and incubated for 15 min in dark. Diluted the cell suspension using 200 μL binding buffer. This suspension was subjected to FACS analysis.

FIG. 8 Showing histogram of Annexin V FITC fluorescence (Logarithmic) versus cell count (linear), here P2 represent the basal fluorescence given to the cells that do not take up the dye (healthy normal cells). P3 represents the cells that have fluoresced on binding with Annexin V FITC (Apoptotic cells). In the MDA MB 231-Control cells (light & dark) most of the cells were observed in P2 population showing normal cells without apoptosis. After PDT with porphyrins of the general formulae 1 a peak shift was observed form P2 to P3 population, indicating Apoptosis.

EXAMPLE 7

Drug Intake Study Using Fluorescence Microscopy.

Seeded mammalian breast cancer cells, MDAMB 231 ($2\times10^5$ cells per plate) with 2 ml DMEM medium and incubated for 24 h. Then added 1 mM of the investigated porphyrin derivatives of the general formulae 1 (stock 100 mM. diluted using DPBS) and incubated for 1 h. The progress of intake of the drug by the cells was then observed though a fluorescent microscope using green filter with time interval of 5 min.

Figure 9:
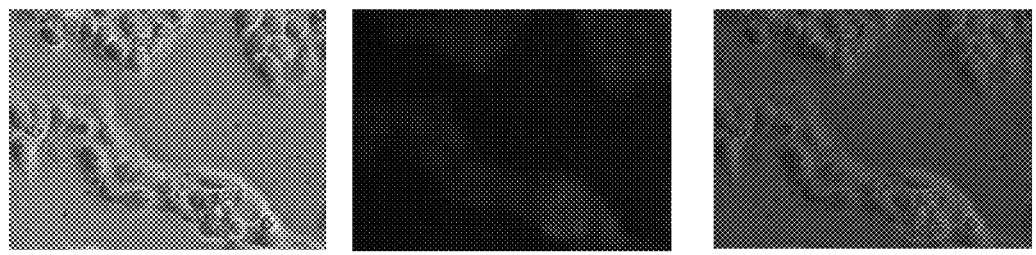

FIG. 9.A showing phase contrast image of MDA MB 231 cells. 4 B showing fluorescent image of MDA MB 231 cells stained with porphyrin derivative of the general formulae 1. 9. C showing perfect merging of image A & B indicating drug intake into cell.

FIG. 10 showing fluorescent images taken at a time interval of 5 minutes with porphyrin derivative of the general formulae 1. From this picture it is evident that up take of porphyrin derivative of the general formulae 1 is occurring within 10 minutes of drug addition in the cell. This suggests the quick intake of the said porphyrin derivative of general formula 1 into cell which predicts the potency of the drug.

EXAMPLE 8

Drug Localization Study (Nuclear Staining).

Seeded mammalian breast cancer cells, MDAMB 231 ($2\times10^5$ cells per plate) with 2 mL DMEM medium and incubated for 24 h. 1 mM of the investigated porphyrin derivatives of the general formulae 1 (stock 100 mM, diluted using DPBS) was then added to the above cells and incubated further for 1 h. The Hoechst dye was then added as the reference and the localization was observed though a fluorescent microscope using UV as well as green filters.

FIG. 11A showing fluorescent image obtained by staining of MDA MB 231 cells with porphyrins derivative of general formulae 1. FIG. 11B showing fluorescent image obtained by staining of MDA MB 231 cells with standard nuclear stain Hoechst. FIG. 11C showing perfect merging which confirmed the nuclear localization property of porphyrin derivative of general formula 1.

Advantages

The porphyrin dyes used for the present invention possess satisfactory properties of a NIR PDT agent and can be used as fluorescent probe in photodynamic therapeutic and diagnostic, biological, biochemical and industrial applications. The main advantages of these systems include:

1. Porphyrin derivatives represented by formula 1 are novel and pure single substances.
2. Their synthetic methodology is very economical.
3. Porphyrin derivatives represented by formula 1 possess absorption in the visible to near-infrared region (400-700 nm).
4. Porphyrin derivatives represented by formula 1 possess fluorescence emission in the near-infrared region (620-740 nm).
5. Porphyrin derivatives represented by formula 1 possess emission quantum yields in the range 0.1-0.2 in aqueous media.
6. Porphyrin derivatives represented by formula 1 possess triplet quantum yields in the range 0.5-0.7 in aqueous media.
7. Porphyrin derivatives represented by formula 1 show better cytotoxicity than the existing clinical photosensitizer FOSCAN.
8. They can be used for photodynamic applications such as sterilization of fluids etc.
9. Porphyrin based dyes can be used as NIR fluorescent probes for protein labeling.
10. Porphyrin based dyes can be used as NIR fluorescent probes for nuclear staining.
11. Porphyrin derivatives of the general formula 1 can be used as NIR fluorescent labels in immunoassays.
12. They can be used for the detection of biologically important metal ions under physiological conditions.
13. These novel dyes can be used as near-infrared fluorescence sensors in biological and industrial applications.

We claim:

1. Porphyrin derivatives of the general formula 1,

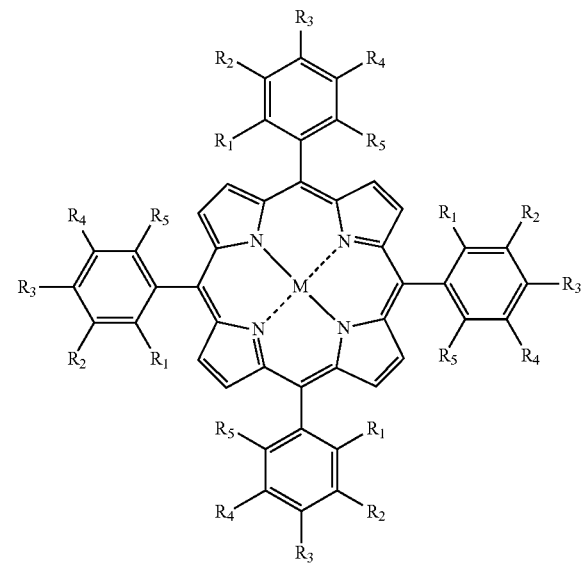

Formula 1 wherein, $R_1$, $R_3$, $R_5$=OH; $R_2$, $R_4$=H; M=2H;

wherein, $R_1$, $R_3$, $R_5$=OH; $R_2$, $R_4$=H; M=Zn,Co, Cu, Fe, Au;

wherein, $R_1$, $R_3$, $R_5$=OH; $R_2$, $R_4$=I; M=2H;

wherein, $R_1$, $R_3$, $R_5$=OH; $R_2$, $R_4$=I; M=Zn,Co, Cu, Fe, Au;

wherein, $R_1$, $R_2$, $R_4$, $R_5$=H; $R_3$=(OCH$_2$CH$_2$)$_n$OH (where n=3-7); M=2H;

wherein, $R_1$, $R_2$, $R_4$, $R_5$=H; $R_3$=(OCH$_2$CH$_2$)$_n$OH (where n=3-7); M=Zn,Co, Cu, Fe, Au.

2. The porphyrin derivative of claim 1, wherein $R_1$, $R_3$, $R_5$=OH; $R_2$, $R_4$=H; M=2H.

3. The porphyrin derivative of claim 1, wherein $R_1$, $R_3$, $R_5$=OH; $R_2$, $R_4$=H; M=Zn.

4. The porphyrin derivative of claim 1, wherein $R_1$, $R_2$, $R_4$, $R_5$=H; $R_3$=(OCH$_2$CH$_2$)$_n$OH (where n=3); M=2H.

5. The porphyrin derivative of claim 1, wherein $R_1$, $R_2$, $R_4$, $R_5$=H; $R_3$=(OCH$_2$CH$_2$)$_n$OH (where n=3); M=Zn.

* * * * *